United States Patent [19]

Frank et al.

[11] Patent Number: 4,689,405

[45] Date of Patent: Aug. 25, 1987

[54] PROCESS FOR THE SIMULTANEOUS SYNTHESIS OF SEVERAL OLIGONUCLEOTIDES ON A SOLID PHASE

[75] Inventors: Ronald Frank, Wolfenbüttel; Wiebke Heikens, Braunschweig, both of Fed. Rep. of Germany

[73] Assignee: Gesellschaft fur Biotechnologische Forschung mbH (GBF), Braunschweig-Stockheim, Fed. Rep. of Germany

[21] Appl. No.: 567,954

[22] Filed: Jan. 4, 1984

[30] Foreign Application Priority Data

Jan. 20, 1983 [DE] Fed. Rep. of Germany ....... 3301833

[51] Int. Cl.[4] ............................................. C07H 19/20
[52] U.S. Cl. ...................................... 536/27; 536/28; 536/29
[58] Field of Search .............................. 536/29, 27, 28

[56] References Cited

U.S. PATENT DOCUMENTS

| | | | |
|---|---|---|---|
| 3,280,104 | 10/1966 | Moffatt et al. | 536/29 |
| 4,373,071 | 2/1983 | Itakura | 536/29 |
| 4,401,796 | 8/1983 | Itakura | 536/29 |
| 4,404,368 | 9/1983 | Alvarado-Urbina | 536/29 |
| 4,458,066 | 7/1984 | Caruthers et al. | 536/29 |
| 4,500,707 | 2/1985 | Caruthers et al. | 536/29 |

*Primary Examiner*—Dale R. Ore
*Attorney, Agent, or Firm*—Kane, Dalsimer, Kane, Sullivan and Kurucz

[57] ABSTRACT

The present invention relates to a process for the simultaneous synthesis of several oligonucleotides on a solid phase by using supports of flat material. Finally, the present invention relates to an apparatus for carrying out said process.

6 Claims, 2 Drawing Figures

PROCESS FOR THE SIMULTANEOUS SYNTHESIS OF SEVERAL OLIGONUCLEOTIDES ON A SOLID PHASE

BACKGROUND OF THE INVENTION

1. Field of the Invention

Apart from in pure research work, chemically synthesised oligonucleotides are being used increasingly in the industrial development of new biotechnological processes. The use of such nucleic acid fragments in the isolation, alteration (mutation) and total synthesis of genes, which carry the information for interesting proteins, or of DNA regions, which are responsible for regulating the expression of these proteins, opens up new possibilities for the microbiological production of such proteins.

2. Brief Description of the Prior Art

In the present context, oligonucleotides should be understood as being oligoribonucleotides and also oligodeoxyribonucleotides. The chemical synthesis of oligonucleotides is carried out in steps by linking suitably protected units or blocks which may comprise one or more nucleotides. Various methods of synthesis, which differ from one another in the chemistry of linking the 3'-5'-phosphodiester bond, belong to the prior art. Examples are:

(A)
- phosphate diester method; cf. Nucleic Acids Research 10 (1982) 6553 to 6570, page 6553, line 10,
- phosphate triester method; cf. locus citatus, pages 6561 to 6562,
- phosphite triester method; cf. locus citatus, page 6563

(B)
- linking of 5'-phosphates to 3'-hydroxyl groups; or
- linking of 3'-phosphates to 5'-hydroxyl groups; cf. locus citatus, page 6561

(C)
- use of mononucleotides as blocks;
- use of dinucleotides as blocks; or
- use of blocks that comprise from more than two nucleotides up to oligonucleotides.

Rapid syntheses are carried out according to the Merrifield principle on a solid phase, the growing chains of the oligomer generally being bonded chemically, by their ends that are not being lengthened, to a solid phase in the form of a macroscopically solid support material. The chain-lengthening reactions or linking reactions are then carried out at the surface of the support material, the reaction product remaining bonded to the support and reaction excesses and reactants being removed by washing.

Hitherto, a large number of support materials have been used for such syntheses, it being necessary for the support material and the method of synthesis to be matched to one another; cf. locus citatus and literature indicated therein. The person skilled in the art is familiar with this matching procedure. Common to all of the support materials employed hitherto is that they are used in the form of granulates. For example, oligonucleotides have hitherto been synthesised individually on a small quantity of granulate. If n oligonucleotides having a chain length of m nucleotide units are to be manufactured according to this prior art, then n×m synthesis steps are necessary.

SUMMARY OF THE INVENTION

The problem of the invention is to provide a process for the simultaneous synthesis of several oligonucleotides on a solid phase, in which the number of synthesis steps can be reduced compared with the prior art. This problem is solved according to the invention by using one or more supports of flat material as the solid phase. Flat material should be understood as being a material in the case of which one of the three spatial dimensions which are perpendicular to one another is substantially smaller than the other two. These supports of flat material are used in any spatially defined form as segments, for example in the form of sheets or strips. The flat material may consist, for example, of cellulose, synthetic material or glass, or of reinforced (especially fibre-reinforced) material of this type. The flat material may be paper based on the mentioned materials. Examples of such flat materials are filter paper and filter paper reinforced with glass fibres. The flat material may be suitable per se for linking to starting nucleotide blocks (such as, for example, cellulose) or it may have been modified for the purpose in a method known to the person skilled in the art, for example from the prior art.

DETAILED DESCRIPTION OF THE PREFERRED EMBODIMENTS OF THE INVENTION

Figure 1:
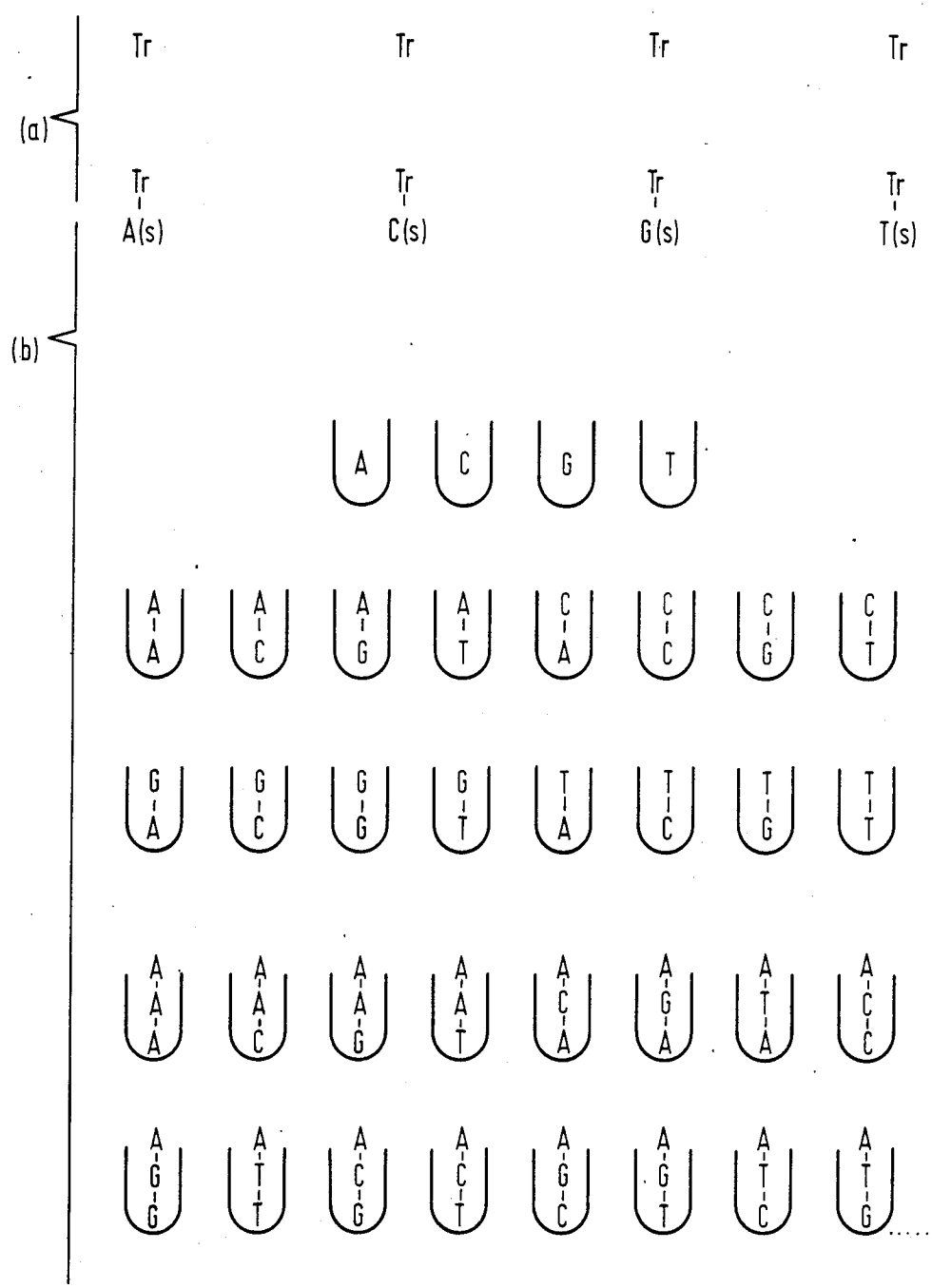
FIG. 1 is a representation of a scheme for carrying out the process of the invention.
Figure 2:
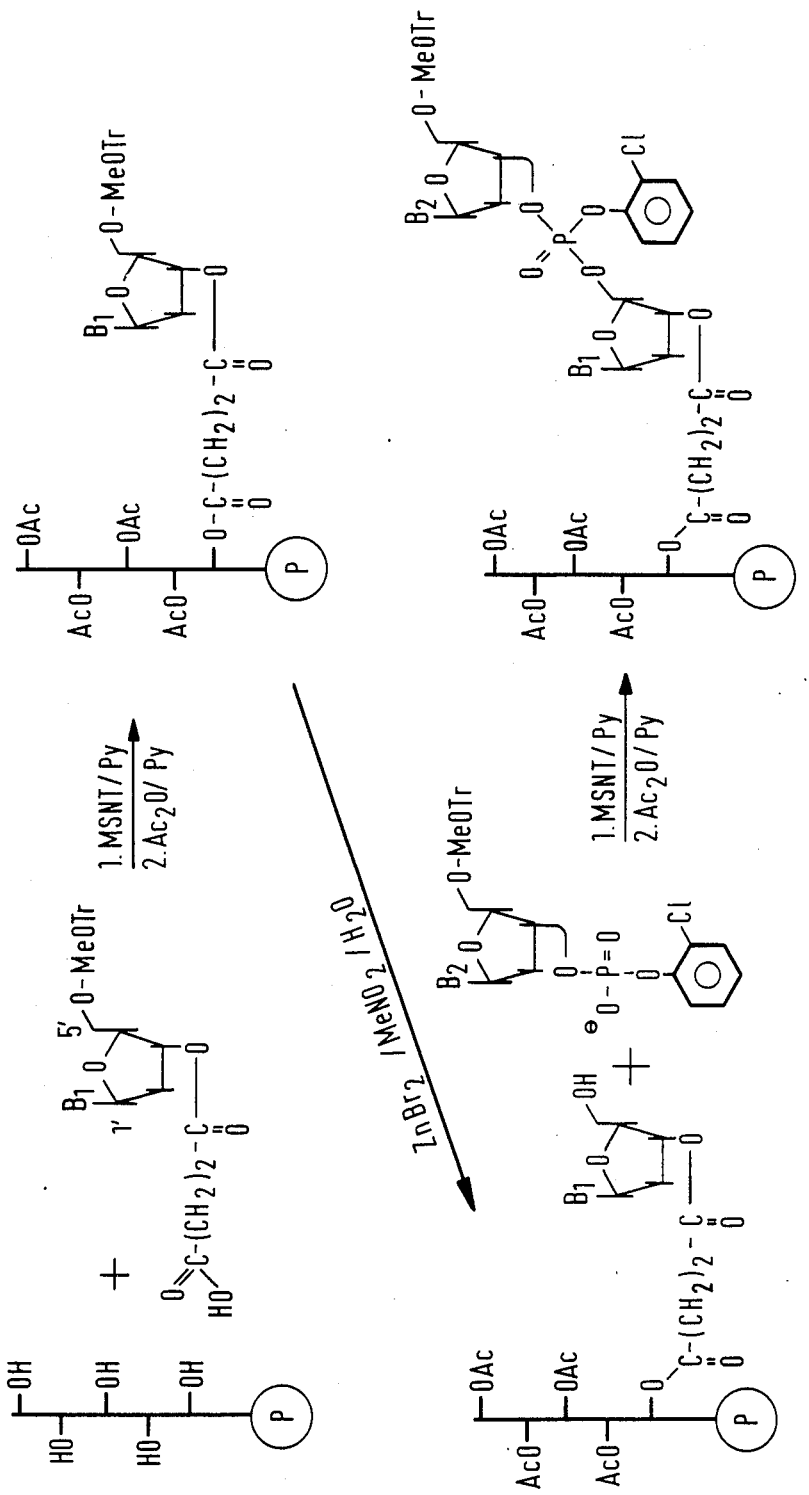
FIG. 2 is a representation of the synthesis of oligodeoxyribonucleotides according to the process of the invention.

According to a preferred embodiment, the flat material used is permeable to the liquid reaction medium and/or to the reactants contained therein.

The use according to the invention of supports of flat material means that several supports can be combined simultaneously in one and the same reaction vessel with one and the same block and can then be cleanly separated from one another again without being contaminated.

For example, in the synthesis according to the invention of oligonucleotides from mononucleotides, the procedure may be such that (a) up to four groups of supports that can be linked to starting nucleotides are used, each group of supports comprising at least one support, and the supports are linked to starting mononucleotides which differ from group to group and (b) up to four liquid reaction media (containing different mononucleotides) are provided and the supports that result from stage (a) and are linked to the starting nucleotides are introduced into the reaction media in groups in accordance with the sequence of the oligonucleotides to be synthesised, and (c) according to the method of synthesis chosen, a deprotection step may precede stage (b) and a blocking step may follow stage (b).

In this procedure, the first nucleotide of the oligonucleotide chain to be synthesised is bonded chemically to the support according to a method which is known per se and which is appropriate for the particular support material. Oligonucleotides generally comprise only four different building components, namely the ribonucleotides A, C, G and U or the deoxyribonucleotides A, C, G and T. If mononucleotides are used as blocks, four groups of support films charged with different starting nucleotides are required and each group may comprise one or more support films. If dinucleotides are used as blocks, $4^2=16$ differently charged support films are required.

Each oligonucleotide is synthesised on the support films of one group of supports or one group of segments. For this purpose, the free functional groups of the support films linked to the starting nucleotides are usually blocked and the starting nucleotides de-protected. Groups of supports, to the supports of which the same block is to be linked, are introduced together into one and the same liquid reaction medium. When using mononucleotide blocks, four different liquid reaction media are necessary. The linking reactions are carried out in accordance with the particular synthesis method applied. After linking has been effected, blocking and de-protection are normally carried out again. The next linking cycle then follows and for this purpose the support films are distributed again in groups in the four different liquid reaction media in accordance with the sequence to be synthesised. After the final linking step, all of the support films are separated and the oligonucleotides are split off from the support films, de-protected and isolated.

If, for example, oligonucleotides are to be built up according to the invention from nucleotide blocks that comprise from 2 to n mononucleotides, n being an integer greater than 2, for example 3 to 8, the procedure may be such that (a) groups of supports that can be linked to starting nucleotides are used, each group comprising one or more supports, and the supports are linked to starting nucleotide blocks that differ from group to group and (b) liquid reaction media containing different nucleotide blocks are provided and the supports that result from stage (a) and are linked to the starting nucleotide blocks are introduced into the reaction media in groups in accordance with the sequence of the oligonucleotides to be synthesised, and (c) according to the method of synthesis chosen, a de-protection step may precede stage (b) and a blocking step may follow stage (b), the particular number of mononucleotides comprised by the starting nucleotide block, the particular number of groups of supports, or reaction media and of mononucleotides comprised by the nucleotide blocks being shown in the following Table:

| Starting nucleotide block comprises mononucleotides | Number of groups of supports up to | Number of reaction media up to | Nucleotide block comprises mononucleotides |
|---|---|---|---|
| 1 | 4 | $4^2$ | 2 |
| 2 | $4^2$ | | |
| 3 | $4^3$ | | |
| . | . | | |
| . | . | | |
| . | . | | |
| n | $4^n$ | | |
| 1 | 4 | $4^3$ | 3 |
| 2 | $4^2$ | | |
| 3 | $4^3$ | | |
| . | . | | |
| . | . | | |
| . | . | | |
| n | $4^n$ | | |

| Starting nucleotide block comprises mononucleotides | Number of groups of supports up to | Number of reaction media up to | Nucleotide block comprises mononucleotides |
|---|---|---|---|
| . | . | . | . |
| . | . | . | . |
| . | . | . | . |
| 1 | 4 | $4^n$ | n |
| 2 | $4^2$ | | |
| 3 | $4^3$ | | |
| . | . | | |
| . | . | | |
| . | . | | |
| n | $4^n$ | | |

According to the process of the invention, the number of synthesis steps for y oligonucleotides having a chain length of z nucleotide units is reduced from $y \times z$ (prior art) to $4 \times z$ (in the case of monomer addition) or from $y \times z/2$ to $16 \times z/2$ (dimer addition) etc. The number of synthesis steps therefore does not depend on y but only on the length of the oligonucleotides to be synthesised and on the block length used.

According to Scheme 1, in stage (a) four supports (Tr) are each linked to a different starting nucleotide (A(s), C(s), G(s) or T(s)). As is shown in Scheme 1, the number of liquid reaction media to be provided in stage (b) depends on the size of the blocks used. According to Scheme 1, four reaction media are required for blocks having one nucleotide each, $4^2=16$ reaction media are required for blocks having 2 nucleotides each and $4^3=64$ reaction media are required for blocks having three nucleotides each; this can of course be extended as desired.

It is therefore possible to use known oligonucleotide synthesis methods for the oligonucleotide synthesis according to the invention. The term "starting nucleotide block" in the present context refers to blocks having one or more nucleotides. In a "starting mononucleotide block" the only nucleotide can be replaced by a nucleoside, and in a "starting oligonucleotide block" especially the first nucleotide bound to the support material can be replaced by a nucleoside. Scheme 2 shows how a support material of cellulose (for example filter paper) is linked to a succinyl starting nucleoside, after which process free OH groups are blocked. Afterwards, the 5'-OH group of the starting nucleoside is de-protected and linked to the 3'-phosphate group of a monomer block after which free OH groups can be blocked again.

The invention is explained in more detail below by means of an Example.

Paper films were used as supports and the starting nucleotides were linked to these films via succinyl bridges. The phosphate triester method with mesitylenesulphonyl nitrotriazolide as the condensation agent was used for the oligomerisation. The monomethoxytrityl group was chosen as the temporary 5'-protecting group that was in each case split off with zinc bromide in nitromethane (1% water). Oligonucleotides having 8 and more nucleotides in the chain were produced. The yields were comparable to those of the prior art.

Explanation of the formula scheme:
P=support material (polymer, in this case cellulose)
$B_n$=nucleobase
N6-benzoyladenine N²-isobutyrylguanine
N⁴-anisoylcytosine
thymine
MeOTr=monomethoxytrityl
MSNT=mesitylenesulphonyl nitrotriazolide
Py=pyridine
Ac=acetyl
MeNO₂=nitromethane

We claim:

1. A process for the simultaneous synthesis of a plurality of different oligonucleotides of predetermined nucleotide sequences on a solid phase, wherein the oligonucleotides are synthesized from mononucleotides, which comprises;
    (a) providing from one to four groups of solid phase supports in the form of segments of flat material, each group of supports comprising at least one support, and the supports are linked to starting mononucleotide building blocks, which differ from group to group;
    (b) providing from one to four reaction media, each containing a different mononucleotide building block;
    (c) contacting the reaction media sequentially with the supports grouped in accordance with the predetermined sequences of the oligonucleotides
    (d) where according to the method of synthesis chosen, a deprotection step may precede stage (c) above and a blocking step may follow stage (c) above.

2. A process according to claim 1, wherein there are used in stage (a) up to $4^n$ groups of supports and oligomeric starting nucleotide building blocks that comprise 2 to n mononucleotides, n being an integer greater than 2.

3. A process for the simultaneous synthesis of a plurality of oligonucleotides of predetermined sequences on a solid phase, wherein oligonucleotides are built up from oligomeric nucleotide building blocks that comprise from 2 to n mononucleotides, n being an integer greater than 2, which comprises;
    (a) providing groups of solid phase supports in the form of segments of flat material, each group of supports comprising at least one support, and the supports of each group are linked to starting nucleotide building blocks that differ from group to group;
    (b) providing from one to $4^n$, reaction media, each containing a different oligomeric nucleotide building block
    (c) contacting the reaction media sequentially with the supports that result from stage (a) above grouped in accordance with the predetermined sequences of the oligonucleotides
    (d) where according to the method of synthesis chosen, a deprotection step may precede stage (c) above and a blocking step may follow stage (c) above and wherein there are one to n number of mononucleotides making up the starting nucleotide building blocks; the number of groups of supports is up to $4^n$, the number of reaction media is up to $4^n$; and the number of mononucleotides making up the oligomeric nucleotide building blocks is from 2 to n; n being a whole number greater than two.

4. A process according to claim 1, 2 or 3, wherein compounds selected from the group consisting of protected nucleosides, nucleotides or oligonucleotides are used as the building block.

5. A process according to claim 4, wherein a fibre-reinforced flat material based on material selected from the group consisting of cellulose, synthetic polymeric material or glass is used.

6. A process according to claim 5, wherein a flat material is used that is permeable to the liquid reaction medium and dissolved compounds contained therein.

* * * * *